United States Patent [19]

Garvie et al.

[11] 4,279,655
[45] Jul. 21, 1981

[54] PARTIALLY STABILIZED ZIRCONIA CERAMICS

[76] Inventors: Ronald C. Garvie, 63 Morey Rd., Beaumaris, Victoria; Richard H. J. Hannink, 143 Huntingdale Rd., Oakleigh, Victoria; Neil A. McKinnon, 22 Stephens St., North Balwyn, Victoria, all of Australia

[21] Appl. No.: 109,711

[22] Filed: Jan. 4, 1980

[30] Foreign Application Priority Data

Jan. 4, 1979 [AU] Australia .............................. PD7274
Apr. 12, 1979 [AU] Australia .............................. PD8379

[51] Int. Cl.³ ...................... C04B 35/48; C01G 25/02; C01G 27/02
[52] U.S. Cl. ...................................... 106/57; 264/65; 423/265; 423/266; 423/608
[58] Field of Search ....................... 423/265, 266, 608; 106/57; 264/65

[56] References Cited

U.S. PATENT DOCUMENTS 3,334,962  8/1967  Clearfield .............................. 423/608
3,514,252  5/1970  Levy et al. ............................. 423/608

OTHER PUBLICATIONS

Rychkewitch, E.; "Oxide Ceramics" Academic Press, New York & London 1960 pp. 354–360.
Rieth, P. et al.; "Fabrication and Flexural Strength of Ultra-Fine-Grained Yttria-Stabilized Zirconia"; Bulletin American Ceramic Society, vol. 55 p. 717, 1976.

*Primary Examiner*—O. R. Vertiz
*Assistant Examiner*—Mark Bell
*Attorney, Agent, or Firm*—Sughrue, Rothwell, Mion, Zinn and Macpeak

[57] ABSTRACT

A magnesia partially stabilized zirconia ceramic material possessing from about 2.8 to about 4.0 wt percent magnesia, and made from a zirconia powder containing no more than about 0.03 percent silica is described. The ceramic material has a microstructure, produced as a consequence of the method by which the material is made, which provides both high strength and good thermal shock resistance properties. This microstructure comprises grains of cubic stabilized zirconia within which are formed, during cooling from the firing temperature, precipitates of tetragonal zirconia. These precipitates are elliptical in shape, with a long axis of about 1500 Angstrom units. Additionally, some of the tetragonal zironcia precipitates are made to transform into a non-twinned microcrystalline monoclinic form of zirconia by reducing the temperature of the material to below 800° C., then subsequently holding the material at a temperature in the range from 1000° C. to about 1400° C. The ceramic material may also contain up to 36 wt percent of hafnia. Such materials can be used for, inter alia, moulds, dies, tappet facings and cutting tools.

14 Claims, 8 Drawing Figures

PARTIALLY STABILIZED ZIRCONIA CERAMICS

This invention concerns oxide ceramic materials made from magnesia partially stabilized zirconia (Mg-PSZ). The materials of the present invention are particularly suited for use as dies for the hot extrusion of metals because they are both strong and possess good thermal shock resistance properties under the conditions which prevail during hot extrusion. However, the materials are not limited to this application; other uses of the material are (non-exhaustively) noted at the end of this specification.

The process of hot extrusion consists of forcing a billet of metal which has been heated, usually to a temperature in the range of 700° C. to 1100° C., through a die (which is normally preheated to about 450° C.) to produce a tube, rod or other extruded product. The die is subjected to both mechanical and thermal stresses and therefore needs to be both physically strong and thermal shock resistant during up-shock to perform its function successfully. The term "up-shock" is used to describe the situation where a material is suddenly exposed to a temperature which is higher than its original temperature; "down-shock" is the reverse situation.

It has been generally accepted that the properties of strength and thermal shock resistance are mutually exclusive in the case of oxide ceramics. For example, fine-grained alumina ceramics are strong but they have poor thermal shock resistance; steel plant refractories are mechanically weak but possess excellent thermal shock resistance. This traditional mutual exclusivity of ideal characteristics remains evident in even the more recently developed zirconia-based ceramics. For example, transformation toughened zirconia ceramics, which are described in the specification of Australian patent application No. 85,680/75 (and also in the paper entitled "Strengthening and microstructural changes in magnesia zirconia alloys" by R. T. Pascoe, R. H. J. Hannink and R. C. Garvie, published in the Proceedings of the Science of Ceramics 9 Conference, Nordwijkerhout, The Netherlands, November 1977), are very strong. They have a modulus of rupture (MOR) of about 600 MPa, but have poor thermal shock resistance, particularly during up-shock. These transformation toughened zirconia ceramics, prepared in both the $CaO-ZrO_2$ and $MgO-ZrO_2$ systems, have essentially two phases, namely pure tetragonal zirconia and cubic stabilized zirconia. The tetragonal phase (metastable at room temperature) exists as precipitate particles of a critical size (about 90 nm in diameter in the $CaO-ZrO_2$ system) distributed in a matrix of cubic stabilized zirconia.

Another recently developed zirconia-based ceramic material is yttria stabilized zirconia, which has been described in the paper "Fabrication and flexural strength of ultra-fine-grained yttria-stabilized zirconia" by P. H. Rieth, J. S. Reed and A. W. Naumann, published in the Bulletin of American Ceramic Society, Vol 55, p. 717, 1976. This ceramic is said to have mainly one phase, a tetragonal zirconia-yttria solid solution in the form of grains about 5 micrometers in diameter. The material is strong (its MOR is about 600 MPa) but it is understood not to have good thermal shock resistance.

Yet another recently developed zirconia-based ceramic material, and one possessing, to the unskilled in this art, a superficial resemblance to the material of the present invention, is the commercial material marketed under the trade name "Zircoa 1706". "Zircoa 1706" is prepared from compositions in the $MgO-ZrO_2$ system. It has been made thermal shock resistant by incorporating into its structure about 20% of pure monoclinic zirconia in the form of large particles, about 25 micrometers in diameter, located at grain boundaries. Thus its thermal shock resistance arises from microcracking and the material has only modest strength, its modulus of rupture being about 207 MPa. It is believed that "Zircoa 1706" would not be a successful die material, even though it is thermal shock resistant, because the mechanical stresses imposed on the die during extrusion are of the order of 415 MPa, which is about twice its original strength. The material "Zircoa 1706" has been described in the paper "Zirconia tailored for thermal shock resistance" published by J. L. Johns and A. G. King in Ceramic Age, Vol 86, p. 29, 1970.

The prime objective of the present invention is to produce a ceramic material which combines both high strength and good thermal shock resistance properties.

This objective is achieved by producing a magnesia partially stabilized zirconia material which has a low silica content and a microstructure which comprises matrix grains of cubic stabilised zirconia, each grain being about 70 micrometers in diameter and containing within it a uniform distribution of very fine microcrystalline monoclinic (MCM) zirconia particles which have been formed by the controlled thermal transformation of tetragonal precipitates of zirconia.

It is believed the presence of MCM zirconia renders propagation of a crack through the material difficult, probably by forcing it to follow a tortuous path. This means that crack propagation through the microstructure is stable, so the material has enhanced thermal shock resistance, especially during up-shock. This form of toughening mechanism, which imparts enhanced thermal shock resistance to the material, is said to be the static toughening mechanism. It should be noted that the monoclinic phase associated with the static toughening mechanism exists *before* the passage of a crack through the material.

The tetragonal precipitates formed within the matrix grains which have not been thermally transformed into MCM zirconia also impart toughness (but not thermal up-shock resistance) to the material because they are transformed mechanically by a moving crack. This phenomenon is termed transformation toughening and is described in the specification of Australian Patent Application No. 85,680/75. Transformation toughening is said to be a dynamic toughening mechanism. It is of secondary importance in the materials which are the subject of this invention. It should be noted that the monoclinic phase associated with this mechanism is observed after the passage of a crack through the material.

According to the present invention, a ceramic material comprises magnesia partially stabilized zirconia having a magnesia content in the range from about 2.8 to about 4.0 wt percent, characterised in that the zirconia powder from which the material has been made contained no more than about 0.03 percent silica and the material has a microstructure comprising a matrix of grains of cubic stabilised zirconia, each grain containing (a) discrete precipitates of tetragonal zirconia, each precipitate having an elliptical shape with the mean length in the long dimension being about 1500 Angstrom units, and (b) discrete precipitates of microcrystalline monoclinic zirconia, produced by controlled thermal transformation of a proportion of the tetragonal zirconia precipitates.

Most of the cubic stabilised zirconia (CSZ) phase has a disordered structure in which there is a random distribution of magnesium and zirconium ions together on the cation sub-lattice and oxygen ions and vacancies together on the anion sub-lattice. A minor amount of the CSZ phase is present as the ordered gamma and/or delta phase in which the oxygen ions and vacancies occupy special positions in the anion sub-lattic.

The MCM microstructure described below is unusual and has never before been reported in the scientific or technical literature. The microcrystalline monoclinic zirconia precipitates, transformed thermally from the parent tetragonal structures, have a fine grain sub-structure of individual monoclinic zirconia blocks slightly misoriented with respect to each other. The blocks have diameters in the range 100–600 Angstrom units and are untwinned. It should be noted that heretofore all monoclinic zirconia ever observed as a constituent of partially stabilised zirconia ceramics has been twinned. Untwinned MCM within CSZ matrix grains is a characteristic and essential microstructural feature of the high performance ceramics which are the subject of this invention.

The preferred magnesia content of the ceramic material is about 3.3 wt percent.

Up to 36 percent by weight of hafnia may be added to the zirconia to increase the working temperature of the ceramic material.

Also according to the present invention, a method of making a magnesia partially stabilized zirconia ceramic material comprises the steps of:

(a) mixing and wet-milling magnesium oxide powder and zirconium dioxide powder containing no more than about 0.03 percent by weight of silica, or materials capable of producing, on firing, magnesium oxide and zirconium oxide with no more than about 0.03 wt percent silica, in proportions such that the effective magnesium oxide content comprises from about 2.8 to about 4.0 wt percent of the mixture and the mean particle size is about 0.7 micrometer;

(b) calcining the powders in the temperature range from about 800° C. to about 1450° C. for about 24 hours;

(c) wet-milling the calcined mixture until the mean particle size is about 0.7 micrometer;

(d) moulding the mixture into a desired shape;

(e) firing the moulded mixture at a temperature in the range from about 1550° C. to about 1800° C.; and (f) cooling the sintered material from the firing temperature to a nucleating temperature in the range between 800° C. and room temperature, the rate of cooling being controlled so that a tetragonal zirconia precipitate phase forms in the sintered material and coarsens to a critical size commensurate with a high strength material;

(g) heating the material immediately after nucleation to an ageing/transformation temperature in the range from 1000° C. to about 1400° C. (alternatively, the nucleated material may be furnace cooled prior to heating to the ageing/transformation temperature);

(h) holding the material at the ageing/transformation temperature for a time sufficient for from 2 to 30 percent of the tetragonal zirconia precipitates to transform into monoclinic zirconia material; and (i) furnace cooling the material to room temperature.

A very low silica content zirconium oxide is necessary as the starting material for the method of the present invention. The use of Harshaw Electronic Grade zirconia, containing from 0.05 to 0.10 wt percent silica and regarded as a low silica material by the zirconia industry, has been found to have a substantially lower strength than the material of the present invention, even though the same method of making the material has been used.

The preferred magnesia content of the ceramic material in step (a) above is 3.3 wt %. The precipitates of tetragonal zirconia in materials with magnesia contents appreciably less than the preferred amount tend to grow too quickly in step (f) above and quality control is difficult to maintain. In materials which have magnesia contents appreciably greater than the preferred amount, the precipitates grow too slowly during step (f) above, adding to the cost of the process.

Improved ceramic materials which are acceptable for many purposes can be produced with the omission of the calcining step (b) and the second milling step (c) of the method defined above. However, the achieved properties of such materials are not as high as those obtainable in materials where the processing steps (b) and (c) are included. For example, the maximum strength and thermal shock resistance (retained strength) of specimens of material prepared by omitting steps (b) and (c) amounted to 596 MPa and 379 MPa, but these values increased to 640 MPa and 638 MPa, respectively, for material prepared with steps (b) and (c) included.

The preferred calcining temperature in step (b) above is about 1050° C. The thermomechanical properties of specimens prepared from batches calcined at temperatures appreciably lower than the preferred value are reduced. Batches calcined at temperatures higher than the preferred value require more extensive milling in step (c), which adds to the cost of the process.

During the mixing and milling steps, the powder mixture is preferably wet-milled with water or with an inert organic liquid until the mean size of the powder particles is about 0.7 micrometer and the powder is reactive and sinterable. If the moulding step is to be performed by cold pressing, a fugitive binder, amounting to about 4 wt percent of the dry powder mix, is usually added at this stage. The mixture is then prepared for moulding by spray drying or by evaporating the liquid phase and granulating the dry powder through a sieve. As an alternative to mixing in this way, physicochemical techniques, such as co-precipitation, sol-gel formation, freeze-drying and co-decomposition of salts, may be used to achieve intimate mixing of oxide powders.

Conveniently, the moulding step of the method of this invention may be performed by cold pressing in a suitable die. However, other moulding techniques may be used, such as isostatic pressing, slip casting or extrusion.

The temperature of firing depends on the magnesia content of the ceramic material. A firing temperature of 1725° C. is preferred for a material containing 3.3 wt percent of magnesia. The phase diagram (see FIG. 7, referred to below) shows that at this temperature, a material of this composition is substantially single phase, homogeneous and cubic. For compositions which have a lower or higher magnesia content than the preferred value, the firing temperature must be adjusted higher or lower, respectively, from 1725° C. to form a substantially single phase, homogeneous and cubic material, in accord with FIG. 7.

A typical cooling rate for step (f) is from 1700° C. to 1400° C. in about 30 minutes and from 1400° C. to 1150° C. in about 90 minutes. At cooling rates appreciably faster than this preferred rate, the product material is susceptible to thermal shock. At cooling rates slower than the preferred rate, the tetragonal precipitates coarsen too quickly, resulting in material with strength and thermal shock resistance properties which are significantly less than the optimum values; also quality control is more difficult.

In order for the controlled thermal transformation of the tetragonal precipitates to occur with ageing in the sub-eutectoid region, prior cooling of the material to at least 800° C. is required, as in step (f). Cooling to this temperature is essential to nucleate the subsequent ageing/transformation reaction.

The preferred temperature in the sub-eutectoid region at which to carry out the controlled ageing/transformation reaction, as in step (g) above, is about 1100° C. When the reaction occurs at temperatures other than the preferred value there is a marked decrease in the thermomechanical properties of the product material.

In step (h) the material is heated at 1100° C. which causes the transformation of tetragonal precipitates to MCM zirconia in a controlled manner. This reaction is allowed to proceed until from about 2 to about 10 wt percent of the material is MCM zirconia; i.e. until about 2 to 30 percent of the tetragonal precipitate particles have been transformed into MCM zirconia. If the amount of transformation of the tetragonal precipitates is less than that described above, the thermal up-shock resistance of the material will not be developed fully. The ageing/transformation reaction time is kept as short as possible consistent with the development of the maximum thermal shock resistance because, occurring simultaneously with it, is the eutectoid decomposition reaction taking place in the grain boundaries. The decomposition reaction results in the formation of a deposit of polycrystalline monoclinic zirconia with grain diameters in the range 1 to 10 micrometers. When the width of the deposit of such monoclinic zirconia in the grain boundaries exceeds about 5 micrometers, there is a marked reduction in the mechanical properties of the material.

MgO-PSZ material fabricated according to the prescription outlined above has unprecedented toughness, strength and thermal shock resistance by virtue of the presence of MCM zirconia within the cubic matrix grains. If the working temperature of the material is at about (or exceeds) 1100° C., much of the MCM zirconia will have transformed to the tetragonal structure and so the enhanced thermomechanical properties of the material will be diminished. In this context, the materials which are the subject of the present invention can be improved by substituting hafnium dioxide (hafnia) for up to 36 wt percent of the zirconia in the composition range 2.8 to about 4.0 wt percent magnesia. This has the effect of raising the transformation temperature of any monoclinic material present whereby preserving the toughening mechanism at high temperatures.

To illustrate the present invention, the features of the sample material prepared to have the preferred composition of the present invention will now be described, with reference to the accompanying drawings, of which.

The pre-firing preparation of the sample of magnesia partially stabilised zirconia material was carried out with two separate batches of material. Each batch was mixed by wet-milling with water and drying by evaporation. One of the batches was calcined and again wet-milled. Both batches were cold pressed into moulds, as described above. Variations of these procedures have been used in the preparation of other samples. For example, the wet-milling has been effected in an inert organic liquid, the drying has been by spray drying, and the consolidation has been carried out by techniques other than cold pressing into moulds.

The zirconia material used to prepare the sample material was Ugine Kuhlmann powder having the following chemical analysis:

| Chemical | wt % |
| --- | --- |
| $ZrO_2 + HfO_2$ | $\geq 99.8$ |
| $Al_2O_3$ | $\leq 0.07$ |
| CaO | $\leq 0.001$ |
| CaO | $\leq 0.001$ |
| Cl | $\leq 0.01$ |
| CoO | $\leq 0.001$ |
| $Fe_2O_3$ | 0.002–0.005 |
| P | $\leq 0.0075$ |
| MnO | $\leq 0.001$ |
| $Na_2O$ | $\leq 0.002$ |
| NiO | 0.005–0.001 |
| $SiO_2$ | $\leq 0.020$ |
| $V_2O_5$ | $\leq 0.001$ |

Similar results were obtained with samples made from Harshaw Electronic Grade zirconia having the following chemical analysis;

| Chemical | wt. % |
| --- | --- |
| $ZrO_2 + HfO_2$ | 99.7 |
| CaO | <0.02 |
| $SiO_2$ | 0.03 |
| $Fe_2O_3$ | <0.015 |
| $Na_2O$ | <0.02 |
| Cl | 0.02 |

| Chemical | wt. % |
| --- | --- |
| SO₄ | 0.06 |

Figure 7:
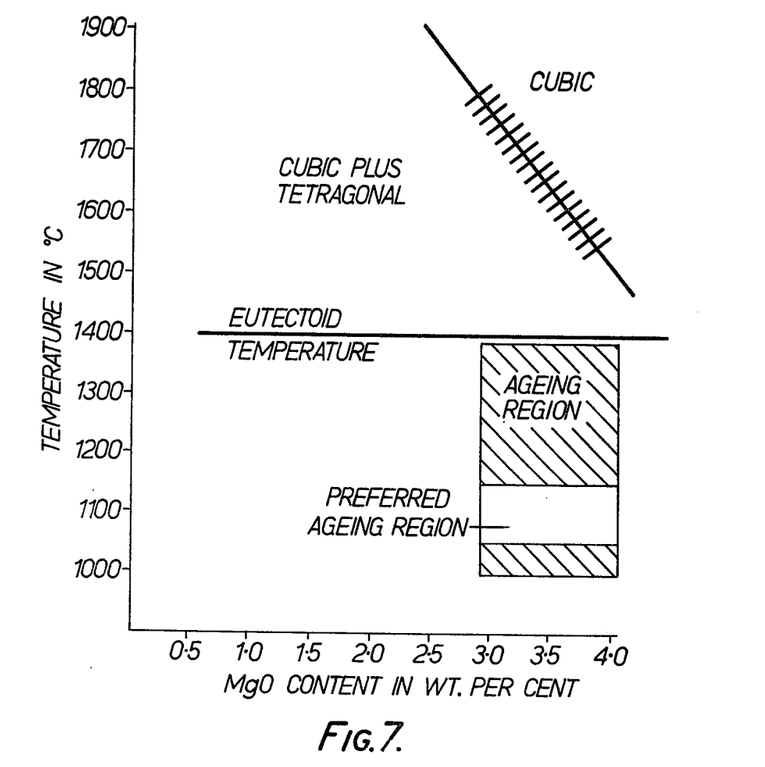
FIG. 7 is a portion of the phase diagram for the MgO-ZrO$_2$ system.

Since the material acquires its controlled microstructure—and hence its strength and thermal shock resistance—during the firing, cooling, nucleating and ageing/transformation steps of the method of this invention, the moulded "green" ceramic material must be fired in a kiln in the neighbourhood of any temperature which would ensure that it develops sintered grains which consist substantially of a single phase which has the cubic fluorite structure. The temperatures required for firing can be seen from FIG. 7 which, as already noted, is a portion of the phase diagram for the MgO-ZrO$_2$ system (the ordinate is temperature and the abscissa is the composition of the ceramic material expressed as wt percent MgO). In FIG. 7, the general range of firing temperatures is indicated by the hatched region located near or in the single phase cubic region. Thus the firing temperature should be in the range of from 1550° C. to 1800° C., depending on the MgO content of the ceramic. In fact, both batches of the sample material were fired at the preferred temperature of firing for a ceramic material containing 3.3 wt percent of MgO (which they did contain), namely at 1725° C. The moulded material should be held at the firing temperature until sintering is complete, which usually means from 1 to 5 hours. In the present example, the firing was for 3 hours.

The development of the controlled microstructure of the ceramic material begins with the controlled cooling of the sintered body from the firing temperature to about 1100° C. The rate of cooling is important and has to be such that a pure tetragonal zirconia precipitate phase forms and coarsens to a critical size (elliptical shape with the mean value of the long dimension about 1500 Angstrom units) when a temperature of about 1100° C. is reached. The material just cooled to this temperature is near its peak strength. As already noted, a typical cooling rate (which was adopted for the fabrication of the sample material) is from 1700° C. to 1400° C. in about 30 minutes and from 1400° C. to 1100° C. in about 90 minutes. Slower rates of cooling may be used, producing useful materials, albeit with properties degraded with respect to material processed according to the preferred method of the present invention. Those skilled in this art will appreciate that it would be more difficult to maintain a uniform high standard of quality in materials produced by using a slower rate of cooling.

The MCM phase must then be "nucleated" by cooling the material at any convenient rate to a temperature in the range from 800° C. to room temperature. This step of cooling to the nucleating temperature is essential; without it, little transformation of the tetragonal precipitates occurs. For example, a specimen containing 3.3 wt percent MgO, fired at 1725° C. and cooled to 1100° C. and held there for 10 hours before being quenched to room temperature had a monoclinic content in its ground surface (GSM) of only about 10 percent. This material disintegrated in the thermal shock treatment described in the next paragraph. A second specimen of identical composition, fired at 1720° C. and cooled at the standard rate continuously to room temperature and then aged at 1110° C. for 10 hours, had about 29 percent GSM; the strength of this material was about 390 MPa after the thermal shock test, which amounted to about 72 percent of its original strength.

Figure 1:
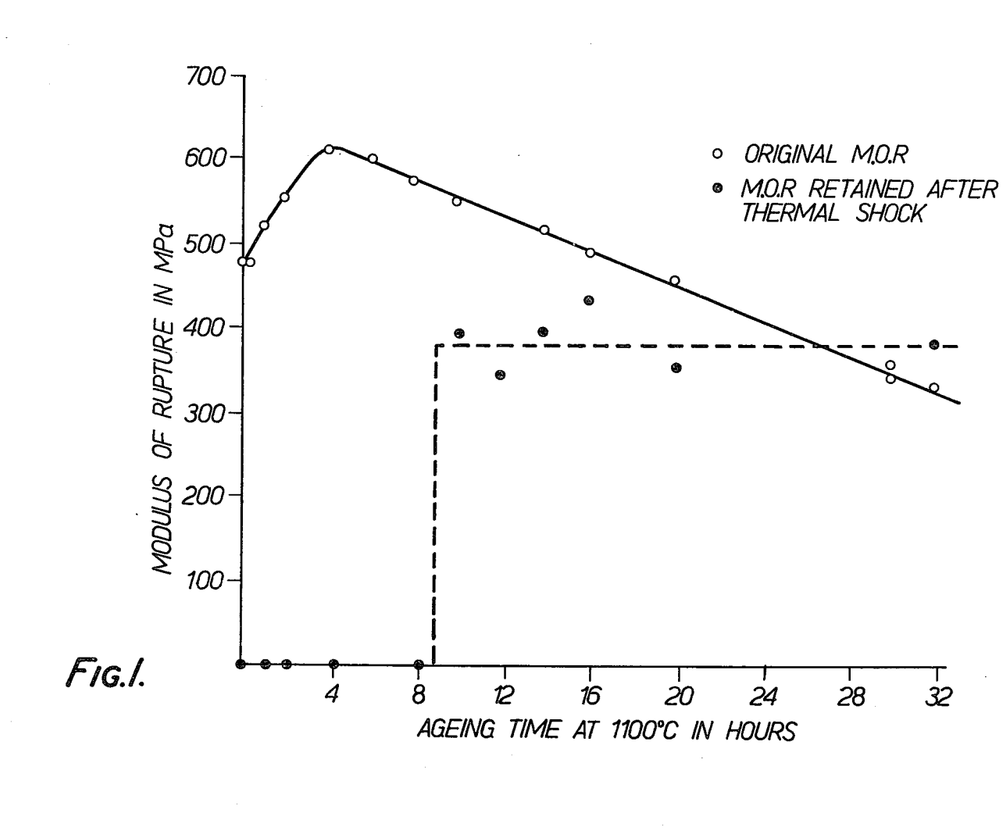
FIGS. 1 and 2 illustrate the effect of ageing time on the strength of partially stabilized zirconia materials of the present invention which have been prepared with the calcining and second milling steps (b) and (c), of the method noted above, omitted (FIG. 1) and with the calcining and second milling steps included (FIG. 2)

FIG. 1 illustrates the importance of the ageing step. It is the ageing/transformation curve (open circles) obtained from specimens of the batch of sample material which was not calcined and given a second wet-milling treatment during its preparation, which, as already noted, contained 3.3 wt percent of MgO. The ageing was performed at 1100° C., after previous cooling of the material to room temperature. The flexural strength in MPa (ordinate) is plotted as a function of the ageing time (abcissa) in hours. Data on the thermal shock resistance (solid circles) of specimens of the same material are also given in FIG. 1. Thermal shock treatment was effected by pre-heating specimens having nominal dimensions 40 mm×3 mm×3 mm to 450° C. and then quenching them into a bath of molten aluminium at 900° C. The important features to note from FIG. 1 are (i) the fact that a significant strengthening of the material occurs during ageing up to 4 hours (the strength increased from 420 MPa for the material in the "as fired" condition to a peak value of 596 MPa after 4 hours of ageing), and (ii) the onset of thermal shock resistance in the material after ageing for approximately 9 hours, as indicated by the high value of the strength retained after thermal shock treatment.

Figure 2:
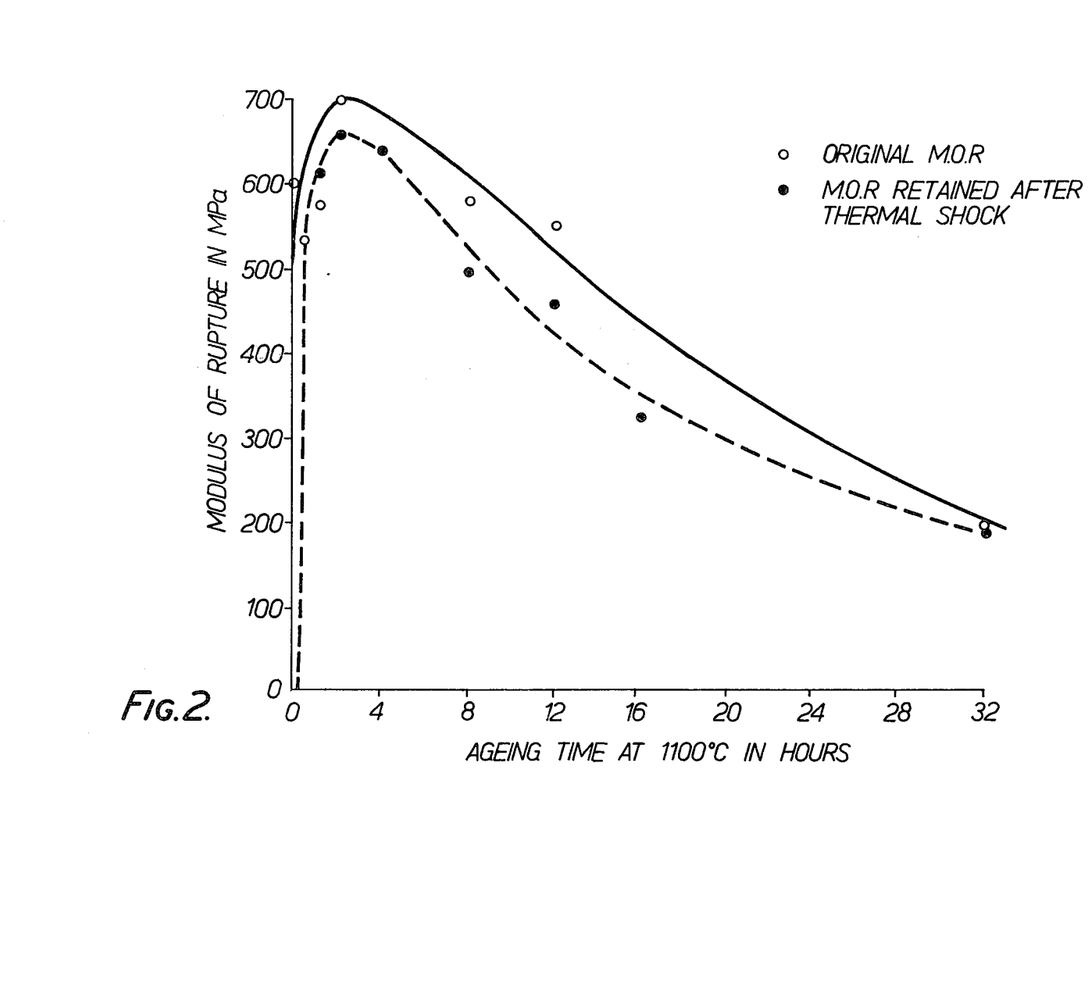

The ageing/transformation times to attain high strength and thermal shock resistance are not fixed but can vary from batch to batch. This is shown in FIG. 2, which presents data obtained from specimens of the sample material which was calcined and given a second wet-milling in its preparation. With this material, thermal shock resistance can be observed after only 1 hour of ageing/transformation at 1100° C. The essential point is that to obtain the best combination of high strength and extreme thermal shock resistance in dense (porosity less than approximately 5 percent) materials of the present invention, some degree of ageing/transformation is required at a temperature in the neighbourhood of 1100° C.

Figure 3:
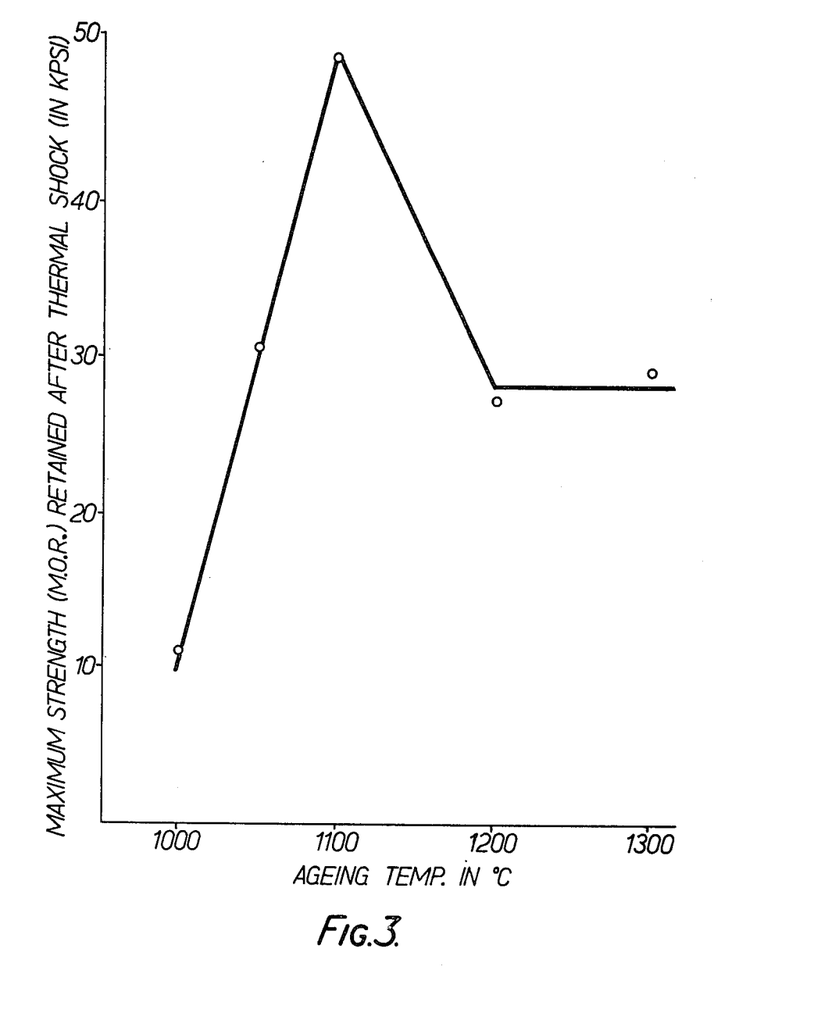
FIG. 3 shows the relationship between the maximum retained strength (thermal shock resistance) and ageing temperatures.

FIG. 3 shows the results that were obtained by ageing specimens from the same batch of sample material at different temperatures, then measuring the thermal shock resistance (which was taken as the observed maximum strength retained after thermal shock treatment). Surprisingly, a strong peak in the retained strength was noted for specimens aged at 1100° C. To explain this, it is believed that when material is aged at temperatures substantially less than 1100° C., the transformation reaction is so slow that even prolonged ageing times produce a conversion of only a small amount of the tetragonal precipitate material into monoclinic material and thus only a modest value of the retained strength; and if material is aged at temperatures significantly greater than 1100° C., the kinetics of the transformation reaction are so fast that the finely balanced microstructure described above is disturbed and again only modest values of the retained strength are produced.

The features of the ageing and thermal shock resistance curves noted above were interpreted by analysing the amount of monoclinic material present on ground surfaces (GSM) and polished surfaces (PSM) of progressively aged specimens using x-ray diffraction (both at room temperatures and at higher temperatures) and optical microscope techniques. Carefully polished surfaces approximate closely to the conditions prevailing within the bulk of the material. Ground surfaces show the effect of stress on transforming any metastable tetragonal phases present in the material. The data obtained from these analyses, which were carried out on specimens from the batch of sample material which did not have the calcination and second wet-milling step in its preparation, are presented in FIG. 3, where the amount of monoclinic phase is plotted as a function of the ageing time at 1100° C.

Figure 8:
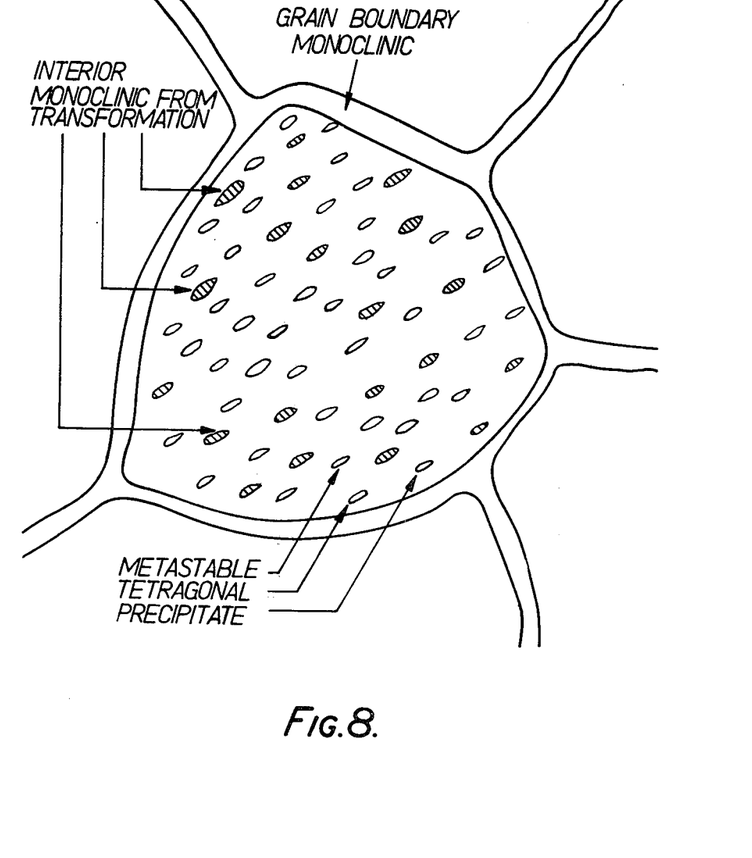
FIG. 8 is a schematic drawing of the microstructure of the thermal shock resistant material.

The conclusions drawn from the data in FIG. 4 will now be discussed in some detail, with reference also to FIG. 8, which is an idealised schematic drawing of a grain showing the presence of phases which are pertinent to the present invention.

The x-ray diffraction analysis of the polished surfaces of the specimens aged from 0 to 8 hours shows that the PSM value (open circles) increases linearly in this interval from about 3 percent to about 12.5 percent. Similar results were obtained using the linear intercept technique on optical micrographs (solid circles), where the only monoclinic phase visible was that found in the grain boundaries. This means that for ageing for this time interval, the only monoclinic material formed in the bulk of the material is that found in the grain boundaries. The grain boundary phase does not impart any thermal shock resistance to the system, as shown by the data given in FIG. 1.

Analyses of the ground surface of the material in the "as fired" condition by x-ray diffraction showed that it has a GSM value of approximately 15 percent. Most of this monoclinic material was produced by the action of grinding, which triggered the tetragonal to monoclinic inversion of metastable precipitate particles. These precipitates and their transformation by stress constitute the sole toughening and strengthening mechanism of the partially stabilised zirconia ceramic which has been aged for up to 9 hours. The GSM value rises fairly steeply to approximately 26.5 percent at about 4 hours of ageing, which coincides with the time required to obtain the peak strength at room temperature. With ageing from 4 to 9 hours, the GSM value remains constant at approximately 26.5 percent. The fact that the initial rate of increase of GSM is greater than the corresponding rate of rise of the PSM value, implies that a different mechanism operates in each case. During the course of ageing at 1100° C. there is no significant coarsening of the precipitate particles to account for the enhanced production of metastable tetragonal zirconia (as determined by GSM values).

The following hypothesis (consistent with observation) is suggested. The precipitates are elliptically shaped and have a range of sizes distributed according to a normal curve about a mean value of 1500 Angstrom units in the long direction. During ageing for a time between 0 and 4 hours, solid state processes occur which alter the misfit parameter which controls the nature of the precipitate/matrix interface; i.e., whether the interface is coherent or is about to exceed its coherency limit. A certain fraction of the precipitate population is thereby changed from having a coherent interface (stable tetragonal structure) to a stage where it is about to lose coherency (metastable tetragonal structure). The newly formed additional metastable particles make an extra contribution to the strengthening of the system. At 4 hours of ageing this fraction of particles has undergone complete conversion to the metastable condition and the GSM value remains constant at 26.5 percent until 9 hours of ageing has occurred.

Consider now material which has been subjected to ageing for 9 to 16 hours. Analysis of the polished surface of such material shows that the PSM value, as measured by x-ray diffraction, increases linearly throughout this interval at the same rate as before. Again, the PSM values derived from x-ray analysis represent an increase in monoclinic content due to the transformation reaction. However the amount of PSM as measured by optical microscopy (i.e., monoclinic zirconia present in the grain boundaries) remains constant at approximately 12.5 percent throughout this interval (see FIG. 3). The discrepancy between the two sets of data means that monoclinic zirconia is now being produced within the matrix grains, probably by transformation of the tetragonal zirconia precipitate phase.

Figure 5:
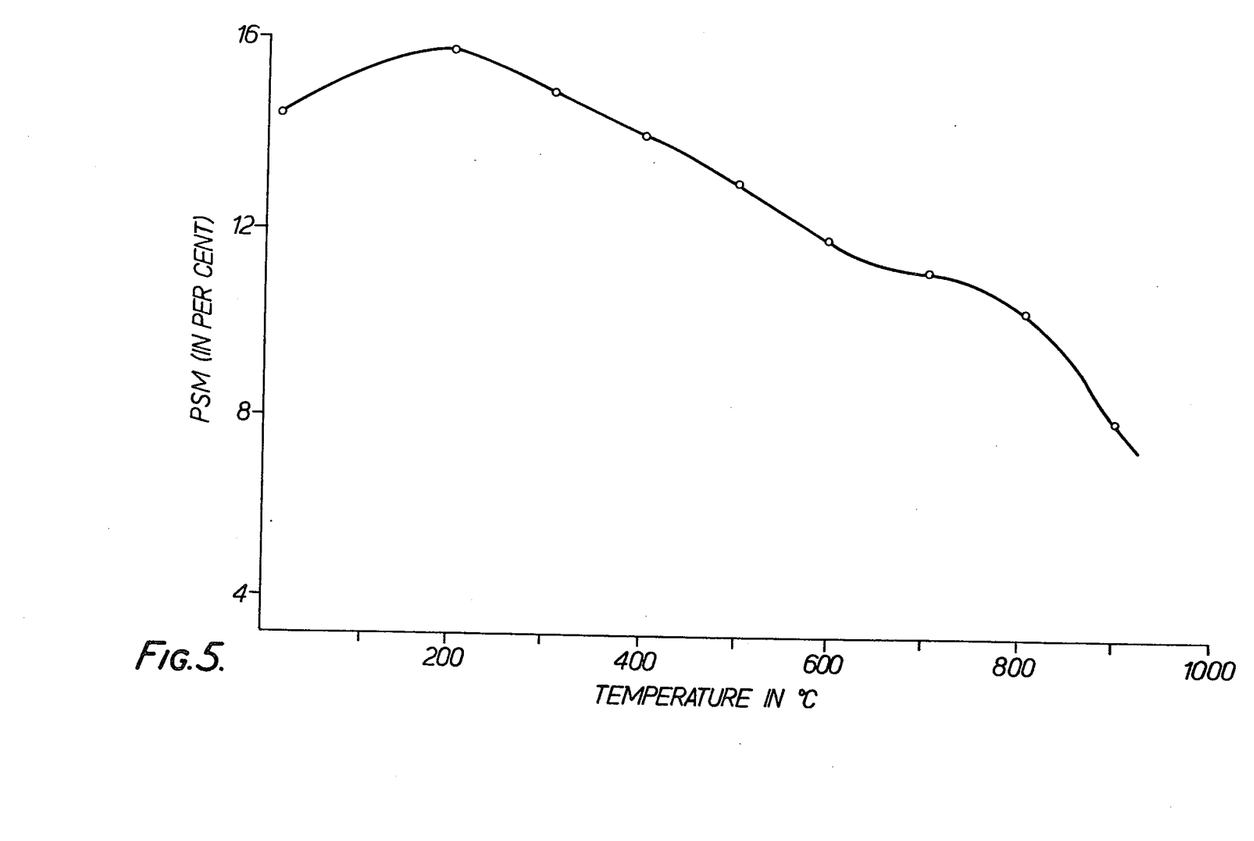
FIG. 5 presents data on the amount of monoclinic phase present on polished surfaces (PSM) of specimens, as determined by x-ray diffraction at various temperatures.

The monoclinic material in the interior of the grain is the important phase concerned with thermal shock resistance. It should be noted that the onset of the discrepancy between the two sets of data (at about 9 hours ageing) coincides with the onset of thermal shock resistance, as noted from FIG. 1. High temperature x-ray diffraction work shows that the monoclinic material in the interior of the grain also has the unusual property of transforming smoothly and continuously to the tetragonal structure as the temperature of the material is increased from 200° C. to 1000° C., as shown by the data given in FIG. 5 for a specimen aged for 16 hours at 1100° C.

Figure 4:
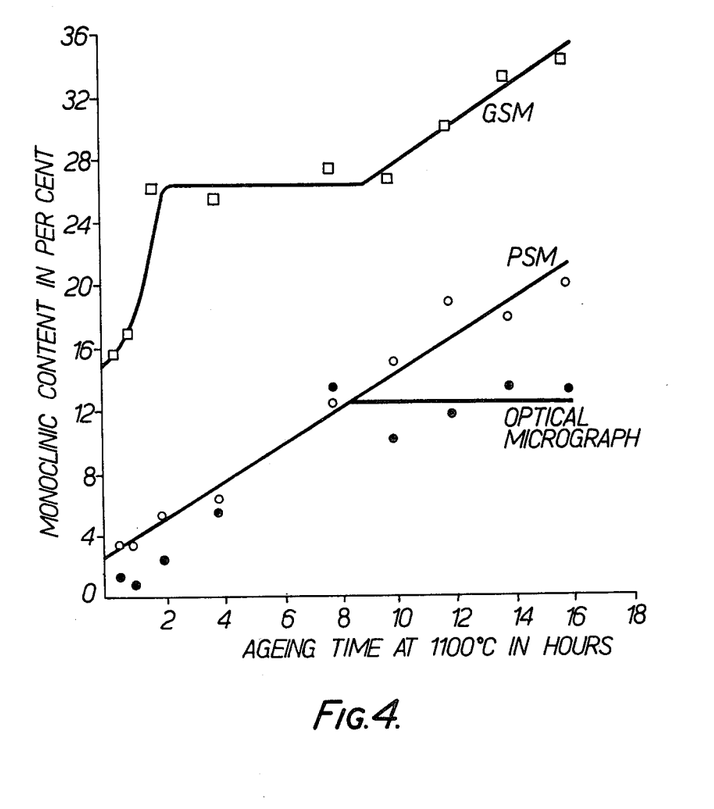
FIG. 4 presents data on the amount of monoclinic phase present on ground surfaces (GSM) and polished surfaces (PSM) of specimens which have been progressively aged at 1100° C., as determined by x-ray diffraction (the term "ground surface" means that the material was machined with a 150 grit diamond wheel at 4200 rpm until about 300 micrometers had been removed; a polished surface is a surface carefully polished with successively finer abrasives down to $\frac{1}{2}$ to 1 micron diamond grit)

Similar examination of the ground surface of specimens of material which has been aged for between 9 and 16 hours shows that the GSM value now increases linearly at about the same rate as the PSM value in this interval (see FIG. 4). The GSM value arises from conversion of the metastable tetragonal zirconia into the monoclinic form by the stresses of grinding (and also from any monoclinic formed during ageing/transformation).

A second possible hypothesis proposed by the present inventors to explain the mechanism of thermal shock resistance is as follows. During up-shock, the outer layers of a specimen are rapidly heated, so that they expand and are placed in compression by the relatively cool interior of the specimen. As the material in the compressive layer is heated, the monoclinic phase within the matrix grains transforms to the tetragonal structure and shrinks in volume by approximately 4 percent. The transformation strain, being opposite in sign to the thermal expansion strain in the heated layers, tends to nullify the latter.

Figure 6:
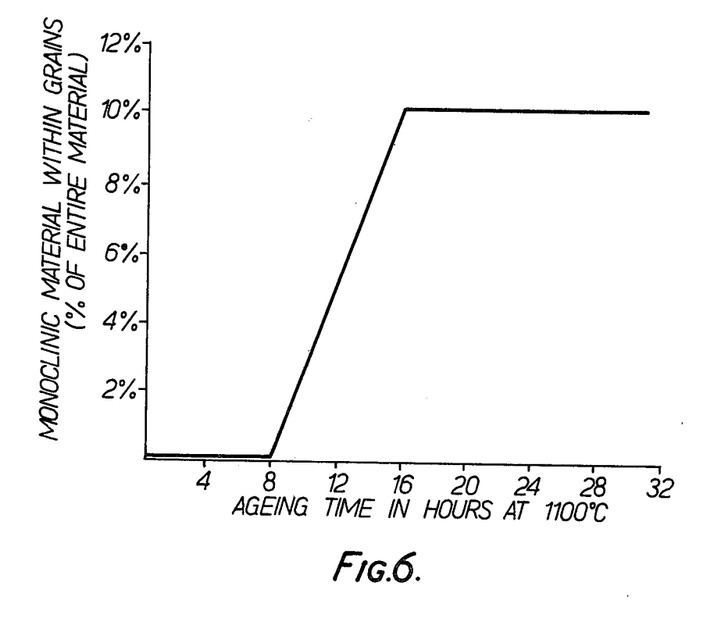
FIG. 6 illustrates the conversion of tetragonal precipitate phase zirconia into MCM zirconia as ageing time is increased.

The difference between the PSM value as measured by x-ray diffraction and optical microscopy (FIG. 4) is a measure of the amount of monoclinic phase formed within the grains. This difference has been plotted as a function of ageing time in FIG. 6. The onset of thermal shock resistance coincides with the first formation of interior monoclinic material, as discussed above. The data of FIG. 6 are in qualitative agreement with the high temperature x-ray data of FIG. 5, although the former data indicate a higher interior monoclinic content than the latter. The reason for this discrepancy is not known.

In summary, the present inventior provides a partially stabilized zirconia ceramic material containing two categories of zirconia which are dispersed simultaneously within grains of cubic zirconia. The two categories are:

(a) tetragonal $ZrO_2$ precipitates metastable at room temperature, which are transformed by stress to the monoclinic structure; although these impart strength and toughness to the system, they are of secondary importance to the materials of the present invention, and (b) monoclinic ZrO₂ material, obtained by conversion of some of the tetragonal precipitate material, with the property of transforming, thermally, back to the tetragonal structure with heating in the temperature range from 200° C. to 1000° C.; this monoclinic material imparts thermal shock resistance to the system and is of primary importance to the materials of the present invention.

A more detailed and semi-quantitative description of the microstructure is as follows:

(a) Dispersed within each grain of cubic zirconia, there are elliptically-shaped precipitates of tetragonal zirconia, having a long dimension of about 1500 Angstrom units. This precipitate phase comprises from 2 to about 10 percent of the material and imparts strength and toughness to the system.

(b) There is a grain boundary phase of monoclinic zirconia amounting to between about 8 and 15 percent of the material. This phase transforms smoothly and continuously to the tetragonal structure in the temperature range 200° C. to 1000° C. This phase is not known to affect the thermomechanical properties of the system; it does not seem to enhance the thermal shock resistance of the system.

(c) There is a monoclinic phase, dispersed within each cubic grain, formed by the transformation of some of the tetragonal precipitates, which comprise from 0.5 to about 20 percent of the system. This phase also transforms to the tetragonal structure smoothly and continuously in the temperature range 200° C. to 1000° C. It is this phase which imparts thermal shock resistance to the system. The MCM phase consists of slightly misoriented untwinned blocks, of dimension from 100 to 600 Angstrom units, existing as sub-grains within the parent (formerly tetragonal) precipitate.

(d) There is the cubic stabilized matrix phase present mainly in its usual disordered form and also as the minor ordered delta and/or gamma phases (both the delta and gamma phases enriched in MgO).

To further exemplify the present invention, the following table (Table 1) summarises the properties of two further batches of material made in accordance with the present invention, including the calcination and second wet-milling step, which had a magnesia content of 3.3 percent by weight and made from a zirconia powder with a silica content of less than 0.03 wt percent.

TABLE 1

| Material (Identified by batch and firing No.) | Strength before thermal shock (MPa) | Maximum strength after thermal shock (MPa) |
|---|---|---|
| V74/B52 | 556 ± 48 | 548 ± 28 |
| V81/B55 | 657 ± 31 | 582 ± 115 |

Table 2, below, shows the properties of a sample of partially stabilised zirconia material having the same magnesia content (3.3 wt percent) but made from zirconia containing between 0.05 and 0.10 wt percent of silica, the preparation stage including the calcination and second wet-milling steps. This material, in common with other materials prepared in accordance with the present invention but using zirconia containing more than about 0.03 wt percent silica, was badly cracked after the firing and/or ageing steps; hence the larger standard deviations in the observations.

TABLE 2

| Material (batch and firing No.) | Ageing time at 1100° C. (hrs) | Strength before thermal shock (MPa) | Strength after thermal shock (MPa) |
|---|---|---|---|
| 69H/2B9 | 0 | 493 ± 50 | 0 |
| | 1.75 | 412 | 234 ± 157 |
| | 4 | 354 | 0 |
| | 6 | 315 ± 100 | 287 ± 92 |
| | 12 | 177 ± 135 | — |

Dies made from the material of this invention have been found suitable for wire-drawing and for hot extruding of brass, copper and steel.

The material of this invention is also suitable for a variety of other wear resistant applications such as (a) the facing surface of tappet facings in automobile engines, especially high power diesel engines, and (b) tool bits for machining metals.

As an example of this last application, a sample of annealed EN26 tool steel was machined with tool bits made of the material of the present invention, containing 3.3 percent magnesia. The tool bits had dimensions 0.5 inch×0.5 inch×3/16 inch with a 0.030 inch radius on each corner and a slight chamfer. They were made from specimens of magnesia partially stabilised zirconia which had been aged at 1100° C. for periods of 0.5 hours, 3 hours and 8 hours. They were tested in a facing test by making a cut of 0.05 inches in the tool steel, at a feed rate of 0.01 inches per rev, the lineal speed of cutting increasing during the test from 393 feet per minute to about 1000 feet per minute. The results obtained, which compare favourably with those from conventional P10 tungsten carbide materials, are shown in Table 3.

TABLE 3

| Sample | Ageing time (hrs) | Retained strength (psi × 10³) | GSM (%) | Fail speed (ft/min) |
|---|---|---|---|---|
| 1 | 0.5 | 55 | 25 | 785 |
| 2 | 0.5 | 0 | 21 | 524 |
| 3 | 3 | 69 | 35 | 885 |
| 4 | 3 | 50 | 30 | 785 |
| 5 | 8 | 55 | 43 | 932 |
| 6 | 8 | 50 | 44 | 1107 |
| 7 | 3.7 | 66 | 36 | 903 |

An interrupted cutting test, using tool bits made from similar materials, was also performed. The test was performed on the circumference of a round bar of EN 26 tool steel containing a 0.5 inch wide slot milled along the length. The test involved making a cut of 0.080 inch at a surface speed of 300 feet per minute and using various feed rates. The tool was considered to have passed the test when it had completed successfully 15 seconds of cutting at the feed rate applied. The results showed that the thermal shock resistant zirconia outperformed commercially available alumina and tungsten carbide (P10 grade) cutting tools at feed rates up to 0.008 inches per second.

A second example of the application of the new material was in the form of dies for wire drawing copper. Such dies were fabricated of the material of the present invention and were tested in a wire drawing machine which was operated at its highest speed. The die was run continuously. The rate of wear of the ceramic die was about one-half that of a cemented tungsten carbide die used in a similar test. When the carbide die was used, the wire drawing machine could not be run at its highest speed nor could it be run continuously. The ceramic die made with MgO-PSZ material containing MCM zirconia did not become hot during the drawing operation whereas the carbide die became very hot. The zirconia die had a very low coefficient of friction with respect to the metal being drawn. Possibly the low coefficient of friction is a consequence of the fact that the MCM material can transform to tetragonal over a wide temperature range. Thus, during the drawing operation, localised transient heating causes the cyclic transformation, monoclinic to tetragonal to monoclinic, in MCM zirconia. This could be the mechanism responsible for the low coefficient of friction.

The wire drawing trial discussed above is the first known successful trial of a zirconia die in such an application.

The invention that has been described above is a mixture of pure zirconia and magnesia powders, treated to produce a ceramic material having a controlled microstructure comprising two kinds of pure zirconia phases, namely:

(1) metastable tetragonal zirconia precipitates which impart toughness and strength to the system, and (2) monoclinic zirconia particles, derived from the controlled transformation of some of the tetragonal zirconia precipitates, which transform over a wide temperature range and impart toughness and thermal shock resistance to the system.

The normal monoclinic to tetragonal transformation temperature of zirconia is approximately 1100° C. At and above this temperature, the valuable properties imparted to the ceramic by the two forms of zirconia discussed above would be lost. For example, if stainless steel were extruded at approximately 1200° C. through dies made from the magnesia partially stabilised zirconia material, one would expect only a limited die life.

As foreshadowed earlier in this specification the upper useful working temperature of the ceramic materials can be extended by using hafnia-zirconia solid solutions instead of pure zirconia. Hafnia has the same crystal structure and polymorphism as zirconia, but its monoclinic to tetragonal inversion occurs at about 1650° C. The two oxides form a homogeneous solid solution series. The transformation temperature of a particular solid solution varies linearly with its hafnia content. Therefore, a ceramic material can be made with a higher working temperature limit by adding hafnia. For example, if sufficient hafnia is added to form a 36 percent by weight solid solution with the zirconia, considering only the non-stabilizing oxides of the system, the working temperature of the resultant ceramic would be about 1230° C. There is little point in adding more than this amount of hafnia because the cubic stabilised matrix phase is ductile in the neighbourhood of 1300° C. Addition of less than this amount of hafnia to the pure zirconia will produce a ceramic material having a working temperature above that of the magnesia partially stabilised zirconia but below 1230° C.

What is claimed is:

1. A ceramic material consisting essentially of magnesia partially stabilised zirconia having a magnesia content in the range from about 2.8 to about 4.0 wt percent, characterised in that zirconia powder from which the material has been made contains no more than about 0.03 wt percent silica and the material has a micro-structure comprising grains of cubic stabilised zirconia, each grain containing (a) discrete precipitates of tetragonal zirconia, each precipitate having an elliptical shape with the mean length in the long dimension being about 1500 Angstrom units, and (b) discrete precipitates of microcrystalline monoclinic zirconia, produced by controlled thermal transformation of a proportion of the precipitates of tetragonal zirconia.

2. A ceramic material as defined in claim 1, in which the discrete precipitates of tetragonal zirconia comprise from 2 to about 10 percent by weight of the ceramic material and the discrete precipitates of monoclinic zirconia comprise from 0.5 to 20 percent by weight of the ceramic material.

3. A ceramic material as defined in claim 1 or claim 2, in which the magnesia content of the material is 3.3 percent by weight.

4. A ceramic material as defined in claim 1 or claim 2, containing also hafnia, the hafnia content of the resulting material comprising up to 36 wt percent of the material.

5. A method of making a magnesia partially stabilised zirconia ceramic material comprising the steps of:
 (a) mixing and wet-milling magnesium oxide powder and zirconium dioxide powder containing no more than 0.03 percent by weight silica, or materials capable of producing, on firing, magnesium oxide and zirconium oxide with no more than 0.03 wt percent silica, in proportions such that the effective magnesium oxide content comprises from about 2.8 to about 4.0 wt percent of the mixture and the mean particle size is about 0.7 micrometer;
 (b) calcining the powders in the temperature range from about 800° C. to about 1450° C. for about 24 hours;
 (c) wet-milling the calcined mixture until the mean particle size is about 0.7 micrometer;
 (d) moulding the wet-milled mixture into a desired shape;
 (e) firing the moulded mixture at a temperature in the range from about 1550° C. to about 1800° C.;
 (f) cooling the sintered material from the firing temperature to a nucleating temperature in the range between 800° C. and room temperature, the rate of cooling being controlled so that a tetragonal zirconia precipitate phase forms in the sintered material and coarsens to an elliptical precipitate having a major axis about 1500 Angstrom units long;
 (g) heating the material immediately after nucleation to an ageing/transformation temperature in the range from 1000° C. to about 1400° C.;
 (h) holding the material at the ageing/transformation temperature for a time sufficient for from 20 to 30 percent of the tetragonal zirconia precipitate to transform into monoclinic zirconia material; and
 (i) furnace cooling the material to room temperature.

6. A method of making a magnesia partially stabilised zirconia ceramic material comprises the steps of
 (a) mixing and wet-milling magnesium oxide powder and zirconium dioxide powder containing no more than 0.03 percent by weight silica, or materials capable of producing, on firing, magnesium oxide and zirconium oxide with no more than 0.03 wt percent silica, in proportions such that the effective magnesium oxide content comprises from about 2.8 to about 4.0 wt percent of the mixture and the mean particle size is about 0.7 micrometer;
 (b) moulding the mixture into a desired shape;
 (c) firing the moulded mixture at a temperature in the range from about 1550° C. to about 1800° C.;

(d) cooling the sintered material from the firing temperature to a nucleating temperature in the range between 800° C. and room temperature, the rate of cooling being controlled so that a tetragonal zirconia precipitate phase forms in the sintered material and coarsens to an elliptical precipitate having a major axis about 1500 Angstrom units long;

(e) heating the material immediately after nucleation to an ageing/transformation temperature in the range from 1000° C. to about 1400° C.;

(f) holding the material at the ageing/transformation temperature for a time sufficient for from 2 to 30 percent of the tetragonal zirconia precipitate to transform into monoclinic zirconia material; and (g) furnace cooling the material to room temperature.

7. A method as defined in claim 5 or claim 6, in which the ageing/transformation temperature is in the range from 1050° C. to 1150° C.

8. A method as defined in claim 7, in which the ageing/transformation temperature is 1100° C.

9. A method as defined in claim 5, in which the rate of cooling of the sintered material is from the firing temperature to about 1400° C. in 30 minutes and from about 1400° C. to about 1150° C. in 90 minutes.

10. A method as defined in claim 5 or 9, in which the effective magnesia content of the ceramic material is 3.3 percent, the firing temperature is 1725° C., and the firing step is carried out for a period from 1 to 5 hours.

11. A method as defined in claim 5, in which, after cooling to the nucleating temperature, the sintered material is cooled in a furnace to ambient temperature before being heated to the ageing/transformation temperature.

12. A method as defined in claim 5 or 11, in which the product ceramic material contains from 2 to about 10 percent by weight of tetragonal zirconia precipitate material and from 0.5 to about 20 percent by weight monoclinic zirconia derived from transformation of the tetragonal zirconia precipitate material.

13. A method as defined in claim 5, in which the mixture of powders of step (a) includes hafnia powder or a material capable of producing hafnia on firing, in such proportion that the product ceramic material contains up to 36 percent by weight hafnia.

14. A ceramic material as defined in claim 3, containing also hafnia, the hafnia content of the resulting material comprising up to 36 wt percent of the material.

* * * * *